US006465489B1

United States Patent
Aulombard et al.

(10) Patent No.: US 6,465,489 B1
(45) Date of Patent: Oct. 15, 2002

(54) UREIDOPIPERIDINE DERIVATIVES AS SELECTIVE HUMAN NK₃ RECEPTOR ANTAGONISTS

(75) Inventors: Alain Aulombard, Lattes; Xavier Emonds-Alt, Combaillaux; Vincenzo Proietto, George d'Orques; Didier Van Broeck, Murviel les Montpellier, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/806,878

(22) PCT Filed: Oct. 4, 1999

(86) PCT No.: PCT/FR99/02355

§ 371 (c)(1),
(2), (4) Date: Apr. 5, 2001

(87) PCT Pub. No.: WO00/21931

PCT Pub. Date: Apr. 20, 2000

(30) Foreign Application Priority Data

Oct. 9, 1998 (FR) ............................................. 98 12859

(51) Int. Cl.⁷ .................. A61K 31/4545; C07D 401/06
(52) U.S. Cl. ...................... 514/316; 546/189; 546/187; 544/129; 514/235.5
(58) Field of Search .............................. 514/316, 235.5; 546/189, 187; 544/129

(56) References Cited

U.S. PATENT DOCUMENTS 5,350,852 A    9/1994   Emonds-Alt et al.
5,674,881 A   10/1997   Edmonds-Alt et al.
5,770,735 A    6/1998   Emonds-Alt et al.
5,942,523 A    8/1999   Bichon et al.

FOREIGN PATENT DOCUMENTS

| CA | 2232007 | 3/1997 |
| EP | 474 561 | 3/1992 |
| EP | 512 901 | 11/1992 |
| EP | 673 928 | 9/1995 |
| WO | 93/18002 | 9/1993 |
| WO | 97/10211 | 3/1997 |
| WO | 98/11090 | 3/1998 |

*Primary Examiner*—Charanjit S. Aulakh
(74) *Attorney, Agent, or Firm*—Paul E. Dupont; Michael D. Alexander

(57) ABSTRACT

The invention concerns compounds of formula (I) in racemic or optically pure form, methods for obtaining them and pharmaceutical compositions containing same. Said compounds are selective NK₃ receptor antagonists.

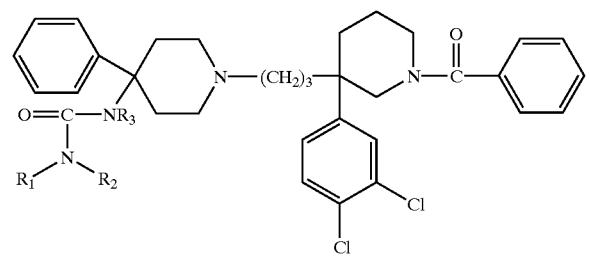

(I)

35 Claims, No Drawings

UREIDOPIPERIDINE DERIVATIVES AS SELECTIVE HUMAN NK₃ RECEPTOR ANTAGONISTS

This application is a 371 of PCT/FR99/02355 filed Oct. 4, 1999, now Ser. No. 00/21931.

The subject of the present invention is new human $NK_3$ receptor selective antagonist compounds for the preparation of medicaments useful in the treatment of psychiatric illnesses, illnesses of psychosomatic origin, hypertension and, in general terms, any central or peripheral pathology in which neurokinin B and the $NK_3$ receptors play a role in interneuronal regulation, a process for obtaining them and pharmaceutical compositions containing them as an active principle.

An illness of psychosomatic origin denotes illnesses with their origin in the central nervous system and their peripheral pathological effects.

In recent years, numerous research studies have been carried out on tachykinins and their receptors. Tachykinins are distributed both in the central nervous system and peripheral nervous system. Tachykinin receptors have been recognized and are classified into three types: $NK_1$, $NK_2$ and $NK_3$. Substance P (SP) is the endogenous ligand of $NK_1$ receptors, neurokinin A ($NK_A$) that of $NK_2$ receptors and neurokinin B ($NK_B$) that of $NK_3$ receptors.

$NK_1$, $NK_2$ and $NK_3$ receptors have been found in various species. For example, $NK_3$ receptors have been identified in guinea pigs, rats and monkeys (Br. J. Pharmacol., 1990, 99, 767–773; Neurochem. Int., 1991, 18, 149–165); they have also been identified in man (FEBS Letters, 1992, 299 (1), 90–95).

A review by C. A. Maggi et al. investigates tachykinin receptors and their antagonists and describe pharmacological studies and applications to human therapy (J. Autonomic Pharmacol., 1993, 13, 23–93).

Patent Application EP-A-0 673 928 describes a family of human $NK_3$ receptor antagonist compounds with the formula:

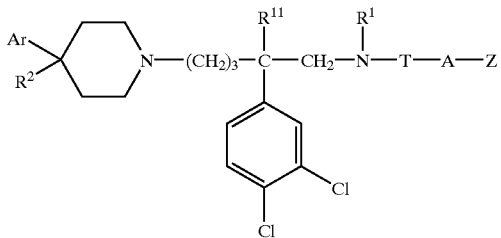

in which $R^1$, $R^{II}$, and $R^2$ have different values.

More particularly, a selective antagonist, (+)-N-[1-[3-[1-benzoyl-3-(3,4-dichlorophenyl) piperid-3-yl]propyl]-4-phenylpiperid-4-yl]-N-methylacetamide hydrochloride, has been described (EP-A-0673 928; Peptides and their antagonists in tissue injury, Montreal, Canada, Jul. 31–Aug. 3, 1994. Canadian J. Physiol. Pharmacol., 1994, 72 (suppl. 2), 25, Abst. III. 0.9.; Life Sci., 1994, 56 (1), 27–32; British Pharmacol. Society, Canterbury, Apr. 6–8, 1995; Eur. J. Pharmacol., 1995, 278 (1), 17–25; 1st Eur. Congress Pharmacol., Milan, Jun. 16–19, 1995).

The subject of Patent Application WO 97/10 211 is compounds with the formula:

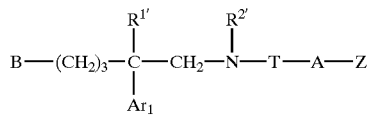

in which B, $R^{1\prime}$, $R^{2\prime}$ and $Ar_1$ take different values. These compounds are described as having a very high affinity for human $NK_3$ receptors.

Non-peptide compounds have now been found which have a very high affinity for human $NK_3$ receptors and marked specificity for the aforesaid receptors plus good bioavailability when administered orally.

Moreover, compounds in accordance with the present invention have good pharmacological activity in animals, decidedly superior to that of (+)-N-[1-[3-[1-benzoyl-3-(3,4-dichlorophenyl) piperid-3-yl]propyl]-4-phenylpiperid-4-yl]-N-methylacetamide.

These compounds can be used for the preparation of medicaments useful in the treatment of psychiatric illnesses or those of psychosomatic origin and all central or peripheral illnesses in which neurokinin B and the $NK_3$ receptor play a role in interneuronal controls.

By very high affinity for human $NK_3$ receptors, we mean an affinity characterized by an inhibition constant Ki which is generally less than $5 \times 10^{-9}$ M.

In ligand fixation studies, the Ki inhibition constant is defined by the Cheng-Prusoff ratio (in Receptor Binding in Drug Research, eds. R. A. O'BRIEN. Marcel Dekker, New York, 1986):

$$Ki = \frac{IC_{50}}{1 + \frac{[L]}{Kd}}$$

[L]: concentration of the ligand,
Kd: dissociation constant of the ligand,
$IC_{50}$: concentration which inhibits 50% of ligand fixation.

By marked specificity for human $NK_3$ receptors, we mean that the inhibition constant (Ki) for human $NK_3$ receptors is generally at least 100 times lower than the inhibition constant (Ki) for $NK_2$ receptors or for $NK_1$ receptors of different species.

The subject of the present invention is compounds with the formula:

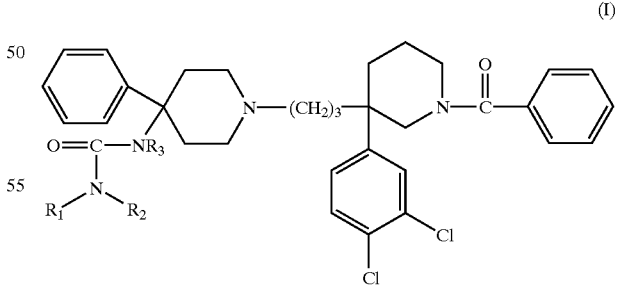

(I)

in which:
R₁ and R₂ each represent, independently of one another, hydrogen or a ($C_1$–$C_3$) alkyl;
or R₁ and R₂ together with the nitrogen atom to which they are bound constitute a heterocyclic radical chosen from among: a pyrrolidin-1-yl, a piperidin-1-yl, a morpholin-4-yl or $R_1$ represents a methyl and $R_2$ represents a methoxy;

$R_3$ represents hydrogen or a $(C_1-C_3)$ alkyl; as well as their salts with mineral or organic acids and their solvates.

Formula (I) compounds, in accordance with the invention, consist of both optically pure isomers and racemic compounds.

Salts of formula (I) compounds can be formed. These salts include both those with mineral or organic acids, which enable a suitable separation or crystallisation of formula (I) compounds, such as picric acid or oxalic acid or an optically active acid, for example a mandelic or camphosulphonic acid, and those which form pharmaceutically acceptable salts, such as hydrochloride, hydrobromide, sulphate, hydrogensulphate, dihydrogenphosphate, methanesulphonate, maleate, fumarate, succinate, naphthalene-2-sulphonate, glyconate, gluconate, citrate, isethionate, benzenesulphonate, paratoluenesulphonate, benzoate. Pharmaceutically acceptable salts are preferred.

In accordance with the present invention, formula (I) compounds are preferred in which $R_1$ and $R_2$ each independently represent hydrogen or a $(C_1-C_3)$alkyl. More particularly, compounds are preferred in which $R_1$ and $R_2$ each independently represent hydrogen or a methyl. Formula (I) compounds in which $R_3$ is hydrogen are preferred in particular.

In accordance with the present invention, optically pure compounds of formula (I) are preferred and very particularly (+) isomers with an (R) configuration.

Thus, in accordance with one of its aspects, the present invention concerns in particular 1-benzoyl-3-(3,4-dichlorophenyl)-3-[3-[4-(N',N'-dimethylureido)-4-phenyl-piperidin-1-yl]propyl]piperidine, as well as its salts and solvates. The (+) isomer of this compound being particularly preferred.

1-Benzoyl-3-(3,4-dichlorophenyl)-3-[3-[4-(N'-methylureido)-4-phenylpiperidin-1-yl]propyl]piperidine and 1-benzoyl-3-(3,4-dichlorophenyl)-3-[3-(4-ureido)-4-phenylpiperidin-1-yl]propyl]piperidine are also preferred, the aforesaid compounds in the form of (+) isomer being particularly preferred.

The subject of the present invention is also a process for the preparation of a formula (I) compound, of its salts and its solvates. This process is characterized in that:

a1) a compound with the formula:

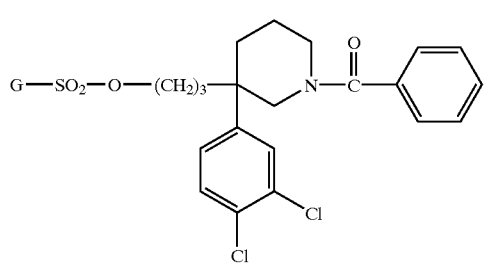

(II)

in which G represents a methyl, phenyl, tolyl or trifluoromethyl group is treated with a piperidine derivative with the formula:

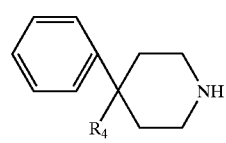

(III)

in which $R_4$ represents an $NR_3CONR_1R_2$ group or a COOH group, $R_1$, $R_2$ and $R_3$ being as defined above for (I);

b1) when $R_4$=COOH the compound thus obtained with the formula:

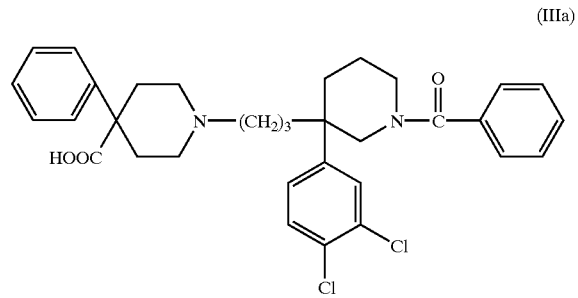

(IIIa)

is converted to a formula (I) compound. optionally, the compound thus obtained at stage a1) or at stage b1) is converted to one of its salts or solvates.

Stage a1) of the process in accordance with the invention is carried out in an inert solvent such as N,N-dimethylformamide, acetonitrile, methylene chloride, toluene, isopropanol or a mixture of these solvents in the presence or absence of a base. When a base is used, this is selected from among organic bases such as triethylamine, N,N-diisopropylethylamine or N-methylmorpholine or from alkali metal carbonates or bicarbonates such as potassium carbonate, sodium carbonate or sodium bicarbonate. In the absence of base, the reaction is carried out using an excess of the formula (III) compound and possibly in the presence of an alkali metallic iodide such as potassium or sodium iodide. The reaction takes place at a temperature between ambient temperature and 100° C.

At stage b1), when compound (III) used in stage a1) of the process contains a carboxyl group COOH, the conversion to a ureido group $NHCONR_1R_2$ takes place in a classical manner through the intermediate formation of an isocyanato —N—C=O group with which the appropriate amine $NHR_1R_2$ is made to react. If need be, the compound obtained is alkylated by a $(C_1-C_3)$ alkyl halide in order to obtain a compound in accordance with the invention in which $R_3$= $(C_1-C_3)$ alkyl.

In accordance with a variant of the process:

a2) a compound with the formula:

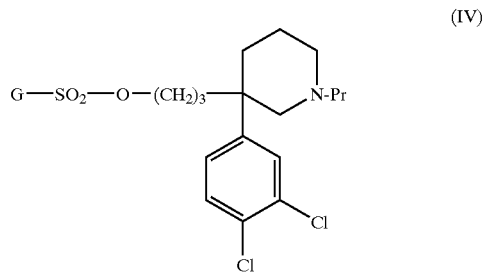

(IV)

in which G is as previously defined and Pr represents a protective group selected from the trityl, tert-butoxycarbonyl or benzyloxycarbonyl group is treated with a piperidine derivative with the formula:

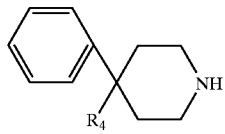
(III)

in which $R_4$ represents an $NR_3CONR_1R_2$ group or a COOH group;

b2) the protective group Pr of the compound thus obtained with the formula:

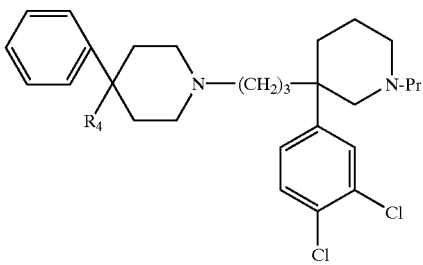
(V)

is selectively eliminated;

c2) the compound thus obtained with the formula:

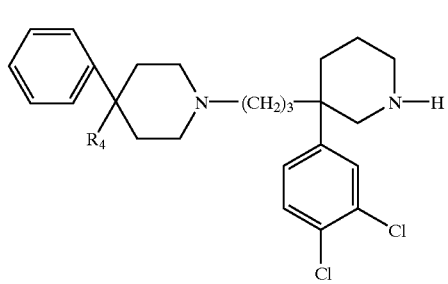
(VI)

is treated with a benzoyl halide;

d2) when the group R4=COOH, the compound thus obtained with the formula:

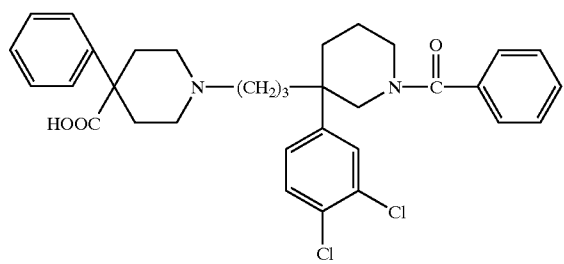
(IIIa)

is converted to a compound with the formula (I).

Optionally, the compound thus obtained in stage c2) or stage d2) is converted to one of its salts or solvates.

At stage b2), deprotection can be undertaken using known professional methods, for example in an acid medium.

According to another variant of the process:

a3) an alcohol with the formula:

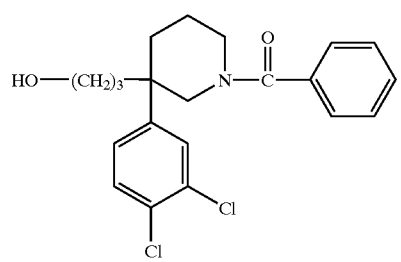
(VII)

is oxidized;

b3) the aldehyde thus obtained with the formula:

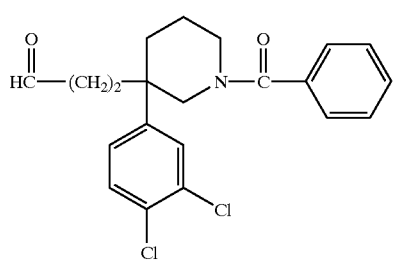
(VIII)

is treated with a piperdine derivative with the formula:

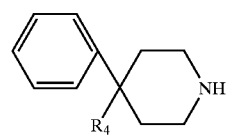
(III)

in which R4 is as defined above;

c3) when $R_4$=COOH, the compound thus obtained with the formula:

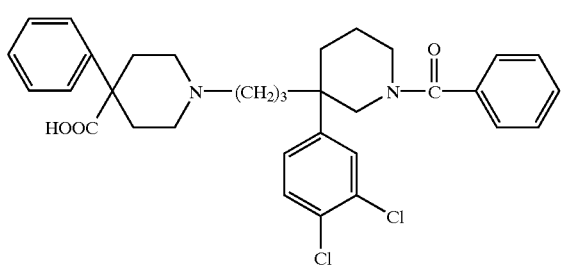
(IIIa)

is converted to a formula (I) compound.

Optionally, the compound thus obtained at stage b3) or stage c3) is converted to one of its salts or solvates.

In accordance with this latter variant of the process, at stage a3), the oxidation reaction is carried out using oxalyl chloride, dimethylsulphoxide and triethylamine for example, in a solvent such as dichloromethane, at a temperature of between −78° C. and room temperature. At stage b3), the formula (III) compound is reacted in the presence of an acid such as acetic acid, in an alcohol solvent such as methanol, to form an imine in situ, which is chemically reduced, using sodium cyanoborohydride for example, or catalytically, using hydrogen and a catalyst such as palladium over charcoal or Raney® nickel.

In accordance with a variant of the process:

a4) a compound with the formula:

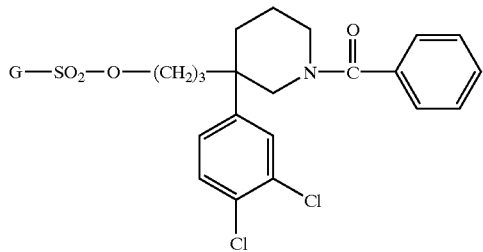

(II)

is treated, in the presence of a base, with a (4-phenylpiperidin-4-ylcarbamic acid ester, preferably the tert-butyl ester, with the formula:

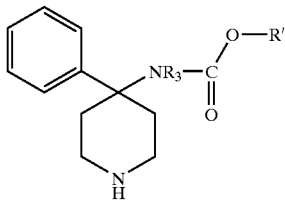

(IX)

in which R'=$(C_1-C_6)$alkyl;

b4) the compound thus obtained with the formula:

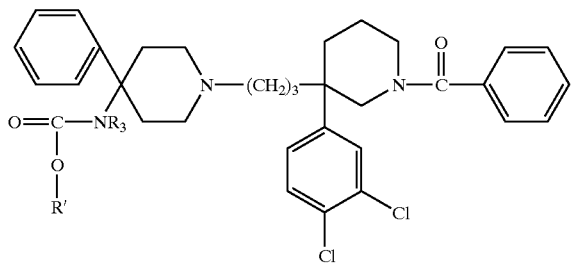

(X)

is deprotected by the action of an acid;

c4) the compound thus obtained with the formula:

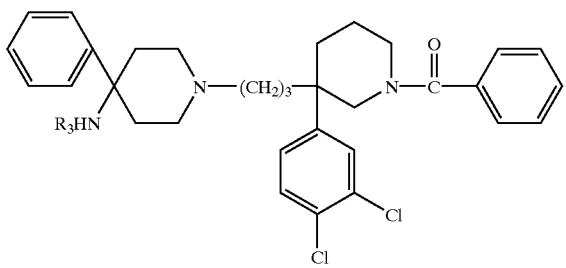

(IX)

is first treated by a reactive derivative of carbonic acid in the presence or absence of a base, then with an amine with the formula $NR_1R_2$, in order to obtain the desired formula (I) compound.

Optionally, the compound obtained is converted to one of its salts or solvates.

In this latter process, it is possible to combine one or more stages. Thus, for example, stages a4) and b4) can be combined in order to directly obtain compound (XI) from compound (II). It is also possible to combine all the stages of the process in accordance with the invention, i.e. not to isolate the intermediate compounds of formula (X) and (XI).

At stage a4), the base used is chosen from among alkali metal hydroxides, such as sodium hydroxide or potassium hydroxide, or from among alkali metal carbonates or bicarbonates such as potassium carbonate or potassium bicarbonate. Potassium carbonate is preferably used.

At stage b4), in order to carry out deprotection, a strong acid is used such as hydrochloric acid, trifluoroacetic acid or formic acid.

Among the reactive derivatives of carbonic acid, 1,1'-carbonyldiimidazole, phosgene or p-nitrophenyl chloroformate is preferred. 1,1'-Carbonyldiimidazole is particularly preferred and, in this case, the reaction takes place in the absence of base.

When phosgene or p-nitrophenyl chloroformate is used, the reaction is carried out in the presence of an organic base such as N,N-diisopropylethylamine, N-methylmorpholine or, preferably, triethylamine.

Finally, in accordance with another variant, a derivative of 4-phenylpiperidine with the formula:

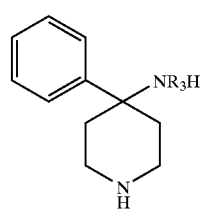

(IXa)

is reacted with the formula (II) compound to directly prepare the formula (XI) compound followed by the stage c4) procedure to prepare the formula (I) compound.

Formula (I) compounds are isolated in the form of free bases or salts using classical techniques.

Thus, when the formula (I) compound is obtained in the form of a free base, salification is achieved through treatment with the chosen acid in an organic solvent. The corresponding salt, which is isolated using standard techniques, is obtained by treatment of the free base, dissolved in an ether such as diethyl ether for example, or in an alcohol such as propan-2-ol or in acetone or in dichloromethane or in ethyl acetate, with a solution of the chosen acid in one of these solvents.

Thus, the following are prepared for example: the hydrochloride, the hydrobromide, the sulphate, the hydrogen sulphate, the dihydrogen phosphate, the methanesulphonate, the oxalate, the maleate, the fumarate, the succinate, the glyconate, the gluconate, the citrate, the isethionate, the benzoate, the naphthalene-2-sulphonate, the benzenesulphonate and the paratoluenesulphonate.

At the end of the reaction, the formula (I) compounds can be isolated in the form of one of their salts, for example hydrochloride; in this case, if necessary, the free base can be prepared by neutralisation of the aforesaid salt with a mineral or organic base, such as sodium hydroxide or triethylamine, or with an alkaline carbonate or bicarbonate, such as sodium or potassium carbonate or bicarbonate.

Formula (II), (IV) and (VII) compounds are obtained using known methods, particularly those which are described in Patent Applications EP-A-0 474 561 and EP-A-0 673 928.

Formula (III) and (IX) piperidines are known or prepared in accordance with known methods such as those described in EP-A-673 928 or WO 96/23787.

The resolution of racemic mixtures of formula (I) compounds enables enantiomers to be isolated. It is, however, preferable to carry out the splitting in two of racemic mixtures from an intermediate compound useful for the preparation of a formula (I) compound such as described in Patent Application: EP-A-0 474 561, EP-A-0 512 901, EP-A-0 591 040 and EP-A-0 673 928.

It is particularly preferable to use a formula (II), formula (IV) or formula (VII) compound as a starting material in an optically pure form.

Thus, in accordance with another of its aspects, the subject of the present invention is a stereospecific process for the preparation of a formula (I) compound having the (R) configuration, of its salts and its solvates, characterized in that a compound with the formula:

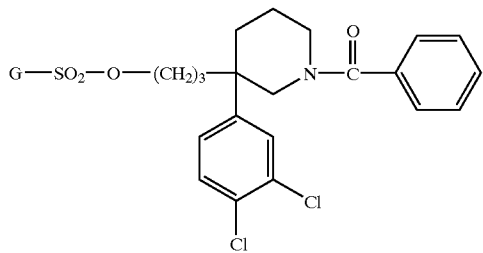

(II)

in which G is as defined above is used, in the form of the (+) isomer, as the starting material, and the reaction is then continued in accordance with stage b1) or, alternatively, in accordance with stages a4) to c4) as described above.

The subject of the present invention is also another stereospecific process for the preparation of a formula (I) compound with the (R) configuration, of its salts and its solvates, characterized in that an alcohol with the formula:

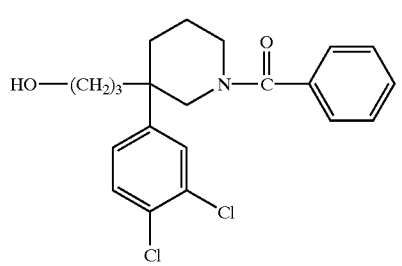

(VII)

in (+) isomeric form is used as the starting material, and the reaction is then continued in accordance with stages a3) to c3) described above.

The subject of the present invention is also a compound with the formula:

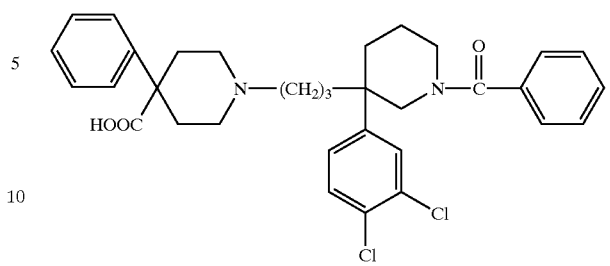

(IIIa)

as well as its salts; in racemic form or in optically pure form, as a key intermediate for the preparation of a formula (I) compound.

Formula (I) compounds above also include those in which one or more hydrogen or carbon atoms have been replaced by their radioactive isotope, tritium or carbon-14 for example. Such labelled compounds are useful in research, metabolic or pharmacokinetic studies and in biochemical tests as receptor ligands.

The affinity of formula (I) compounds for tachykinin receptors has been evaluated in vitro by several biochemical tests using radioligands:

1°) The binding of [$^{125}$I] BH-SP (P substance labelled with 125 iodine with the aid of the Bolton-Hunter reagent) to NK$_1$ rat cortex receptors, to the ileum of the guinea pig and human lymphoblastic cells (D. G. Payan et al., J. Immunol., 1984, 133, 3260–3265).

2°) The binding of [$^{125}$I] His-NKA to NK$_2$ rat duodenum receptors or guinea pig ileum.

3°) The binding of [$^{121}$ ] His [MePhe$^7$] NK$_B$ to NK$_3$ receptors of the cerebral cortex of the rat, the cerebral cortex of the guinea pig and cerebral cortex of the gerbil as well as to cloned human NK$_3$ receptors expressed by CHO cells (Buell et al., FEBS Letters, 1992, 299, 90–95).

Trials were conducted in accordance with X. Emonds-Alt et al. (Eur. J. Pharmacol, 1993, 250, 403–413).

Compounds in accordance with the invention markedly inhibit the binding of [$^{125}$I] His [MePHe$^7$] NK$_B$ to NK$_3$ cerebral cortex receptors of the guinea pig and gerbil as well as to human cloned NK$_3$ receptors: the inhibition constant Ki is generally less than $5 \times 10^{-9}$ M. For the same compounds, it has been found that the inhibition constant (Ki) for rat cerebral cortex NK$_3$ receptors is usually greater than $10^{-8}$ M and that the inhibition constant (Ki) for the rat duodenum NK$_2$ receptor and rat cortex NK$_1$ receptors is generally greater than or equal to $10^{-7}$ M.

Compounds in accordance with the present invention have also been evaluated in vivo in animal models.

In the gerbil, rotational behaviour is induced with the intrastriatal administration of a specific NK$_3$ receptor agonist: senktide; it has been found that a unilateral application of senktide into the striatum of the gerbil leads to marked contralateral rotations which are inhibited by compounds in accordance with the invention administered either via the peritoneum or orally. In these tests, compounds in accordance with the invention are active at doses varying from 0.1 mg to 30 mg per kg.

This result shows that compounds in accordance with the invention pass through the blood-brain barrier and that they can block, at the level of the central nervous system, actions specific to NK$_3$ receptors. They may thus be used for the treatment of any central NK$_B$-dependent pathology, such as psychiatric disorders, or any pathology mediated centrally by the $NK_3$ receptor, such as psychosomatic disorders.

In guinea pigs, the effect on the bronchitic and cough response induced by citric acid has been studied using the model described by S. Daoui et al., in Am. J. Resp. Crit. Care Med., 1998, 158, 42–48. In this test, the Example 10 compound has shown an activity 10 times greater than that of osanetant.

Compounds of the present invention are usually administered in unit dosage form. The aforesaid dosage units are preferably formulated in pharmaceutical compounds in which the active principle is mixed with a pharmaceutical excipient.

In accordance with another of its aspects, the present invention involves pharmaceutical compositions containing, as the active principle, a formula (I) compound or one of its pharmaceutically acceptable salts and solvates.

Formula (I) compounds and their pharmaceutically acceptable salts can be used at daily doses of 0.01 to 100 mg per kg of mammal body weight for treatment, preferably at daily doses of 0.1 to 10 mg/kg. In humans, the dose can vary preferably from 0.5 to 4,000 mg per day, more especially from 2.5 to 1,000 mg according to the age of the subject requiring treatment or the type of treatment: prophylactic or therapeutic. Even though these dosages are examples of an average situation, there may be particular cases where higher or lower doses may be appropriate, such dosages also belong to the invention. In accordance with usual practice, the appropriate dosage for each patient is established by the physician according to age, body weight and the response of the aforesaid patient.

According to another of its aspects, the present invention concerns the use of formula (I) compounds, or one of their pharmaceutically acceptable salts and solvates for the preparation of medicaments intended for the treatment of any pathology where neurokinin B and human $NK_3$ receptors are involved.

Diseases for the treatment of which the compounds and their pharmaceutically acceptable salts can be used are, for example, central nervous system diseases such as diseases associated with dopaminergic system dysfunction, such as schizophrenia, Parkinson's disease, diseases associated with noradrenergic and serotoninergic system dysfunction such as anxiety, panic attacks, concentration disorders, mood disorders, particularly depression, as well as all types of epileptic disorders, in particular Grand Mal epilepsy, dementia, neurodegenerative diseases and peripheral illnesses in which the role of the central nervous system and/or peripheral nervous system takes place via neurokinin B acting as a neurotransmitter or neuromodulator such as somatic disorders related to stress, pain, migraine, acute or chronic inflammation, cardiovascular disorders—hypertension in particular, heart failure, and rhythmic disorders, respiratory disorders (asthma, rhinitis, cough, chronic obstructive bronchitis, allergies, hypersensitivity), gastrointestinal system disorders such as oesophageal ulceration, colitis, gastritis, disorders related to stress (stress-related disorders), irritable bowel syndrome (IBS), irritable bowel disease (IBD), acid hypersecretion (acidic secretion), emesis/nausea (following chemotherapy or postoperative, due to travel sickness or vestibular disorders), food allergies, emesis, vomiting, nausea, travel sickness, diarrhoea, urinary tract disorders (incontinence, neurological bladder), immune system disorders (rheumatoid arthritis), and, more generally, any neurokinin B-dependent pathology.

In the pharmaceutical compositions of the present invention for oral, sublingual, inhaled, subcutaneous, intramuscular, intravenous, transdermic, local or rectal administration, the active principles can be administered in unit forms of administration, in mixtures with standard pharmaceutical media, to animals and to human beings. The appropriate unit forms of administration consist of oral forms such as tablets, gelatin capsules, powders, granules and solutions or oral suspensions, sublingual and buccal forms of administration, aerosols, topical forms of administration, implants, subcutaneous, intramuscular, intravenous, intranasal or intraocular forms of administration and rectal forms of administration.

When a solid composition is prepared in the form of tablets, a wetting agent such as sodium lauryl sulphate can be added to the active principle, micronized or otherwise, and the whole mixed with a pharmaceutical carrier such as silica, gelatine, starch, lactose, magnesium stearate, talc, gum arabic or the like. Tablets can be coated with saccharose, various polymers or other appropriate materials, or treated in such a way that they have a prolonged or delayed activity and can release a predetermined quantity of active principle in a continuous fashion.

A gelatin capsule preparation is obtained by mixing the active principle with a diluent such as glycol or an ester of glycerol and by incorporating the mixture obtained in soft or hard gelatin capsules.

A preparation in the form of syrup or elixir can contain the active principle in combination with a sweetener, preferably calorie-free, methylparaben and propylparaben as an antiseptic, as well as a taste enhancer and an appropriate colouring agent.

Powders or granules dispersible in water can contain the active principle in a mixture with dispersing agents, wetting agents or suspension agents such as polyvinyl-pyrrolidone, likewise with sweeteners or taste correctors.

For rectal administration, suppositories are used, which are prepared with binding agents which dissolve at rectal temperature, such as cocoa butter or polyethylene glycols.

For parenteral, intranasal or intraocular administration, aqueous suspensions, isotonic saline solutions or sterile and injectable solutions are used, which contain dispersing agents and/or pharmacologically compatible dissolving agents, for example propylene glycol or butylene glycol.

Thus, in order to prepare an aqueous injectable solution for intravenous use, a co-solvent can be used such as an alcohol, ethanol for example, or a glycol such as polyethylene glycol or propylene glycol and a hydrophilic surfactant such as Tween® 80. In order to prepare an oily injectable solution via the intramuscular route, the active principle can be dissolved in a triglyceride or a glycerol ester.

For topical administration, creams, ointments and gels can be used.

For transdermal administration, patches can be used in multilaminated forms or as a reservoir in which the active principle can be in an alcoholic solution.

For administration by inhalation, an aerosol is used, also containing sorbitan trioleate or oleic acid for example as well as trichlorofluoromethane, dichlorofluoro-methane, dichlorotetrafluoroethane or any other biologically compatible propulsion gas; a system containing the active principle alone or in combination with an excipient in the form of a powder can also be used.

The active principle can also be present in the form of a complex with a cyclodextrin, for example α, β, γ-cyclodestrin, 2-hydroxypropyl-β-cyclodextrin and methyl-β-cyclodextrin.

The active principle can also be formulated in the form of microcapsules or microspheres, possibly with one or more carriers or additives.

Implants can be used among the slow release forms useful in the case of long-term treatment. These can be prepared in the form of an oily suspension or in the form of microspherical suspension in an isotonic medium.

In each dosage unit, the active principle of formula (I) is present in quantities adjusted to the daily dosages foreseen. In general, each dosage unit is suitably adjusted according to the dosage and the type of administration foreseen, for example tablets, capsules and similar, sachets, ampoules, syrups and similar, drops such that a given dosage unit contains 0.5 to 1,000 mg of active principle, preferably from 2.5 to 250 mg, to be administered one to four times a day.

The aforesaid compositions can also contain other active substances useful for the desired therapy, such as bronchodilators, antitussives, antihistaminics, anti-inflammatories, corticosteroids, anti-emetics, chemotherapy agents.

Thanks to their very high affinity for $NK_3$ human receptors, and their marked selectivity, compounds in accordance with the invention may be used in radiolabelled form as laboratory reagents.

For example, they permit the characterization, identification and the localization of the human $NK_3$ receptor in tissue sections, or of the $NK_3$ receptor in whole animals by means of autoradiography.

Compounds in accordance with the invention also permit the selection or screening of molecules according to their affinity for the human NK3 receptor. This is implemented then by a displacement reaction of the radiolabelled ligand, the subject of the present invention, from its human $NK_3$ receptor.

The following abbreviations are used in the preparations and in the examples:

Ether: diethyl ether
Iso ether: di-isopropyl ether
DMF: dimethylformamide
DMSO: dimethyl sulphoxide
DCM: dichloromethane
THF: tetrahydrofuran
AcOET: ethyl acetate
Boc: tert-butoxycarbonyl
AcOH: acetic acid
hydrochloric ether: saturated solution of hydrochloric acid in ether
BOP: benzotriazol-1-yloxytris(dimethylamino) phosphonium hexafluoro-phosphate
DBU: 1,8-diazabicyclo[5.4.0]undec-7-ene
pH2 buffer: buffer solution marketed by Merck (DARMSTADT)
F: melting point
Eb: boiling point
TA: ambient (room) temperature
silica H: 60H silica gel marketed by Merck (DARMSTADT)
The rotatory power (αD) is measured at 25° C.
NMR: nuclear magnetic resonance recorded at 200 MHz in the DMSO-d6
δ: chemical shift; s: singlet; se: enlarged singlet;
sd: split singlet; d: doublet; t: triplet; qd: quadruplet; sept: septuplet; mt: multiplet; m: unresolved complex.
Pd/C: palladium on charcoal
PTSA: para-toluenesulphonic acid
LDA: lithium disopropyl amide

PREPARATION 1

4-(N',N'-Dimethylureido)-4-phenylpiperidine p-Toluenesulphonate

A) 4-Amino-1-benzyl-4-phenylpiperidine Dihydrochloride.

The starting material is 4-acetylamino-1-benzyl-4-phenylpiperidine prepared in accordance with EP-A-0 474 561.

30 g of 4-acetylamino-1-benzyl-4-phenylpiperidine and 58 ml of HCl concentrated in 135 ml of water are refluxed for 48 hours. The mixture is evaporated and then taken up using EtOH 100 and toluene and evaporated again. The foam obtained is dissolved in 50 ml of MeOH, then left to crystallize by the addition of 250 ml of acetone. 20.5 g of the desired compound are obtained.

B) 1-Benzyl-4-(N',N'-dimethylureido)-4-phenylpiperidine p-Toluenesulphonate 6 g of the compound obtained from the preceding stage and 7.14 g of triethylamine are mixed at room temperature in 50 ml of 1,2-dichloroethane. 1.9 g of N,N-dimethylcarbamoyl chloride are added dropwise in 10 ml of dichloroethane and refluxed for 8 hours. A few drops of triethylamine are added and the reflux is maintained for an additional 3 hours. Concentration is carried out under a vacuum, the residue is extracted in DCM, the organic phase is washed with water, a 10% solution of NaOH, water and a saturated solution of NaCl: the substance is dried on $MgSO_4$ and evaporated and the residue is chromatographed on silica by eluting with DCM/MeOH from (99/1; v/v) to (96/4; v/v). 1.8 g of the desired compound are obtained.

C) 4-(N',N'-Dimethylureido)-4-phenylpiperidine p-Toluenesulphonate 1.8 g of the compound obtained from the preceding stage are dissolved in 150 ml of EtOH 95. 1.11 g of p-toluenesulphonic acid are added and the mixture is hydrogenated at 40° C. under atmospheric pressure in the presence of 1 g of 10% Pd/C. The mixture is filtered on Celite®, evaporated, taken up twice in acetone and evaporated. It is dissolved in 25 ml of acetone, then precipitated in 200 ml of ether in order to obtain 1.86 g of the desired compound in the form of a white solid, F=120–122° C.

PREPARATION 2

4-Phenyl-4-(N'-methylureido)piperidine Benzenesulphonate

A) 1-Benzyloxycarbonyl-4-phenylpiperidine-4-carboxylic Acid.

Dissolve 3.77 g of 4-phenylpiperidine-4-carboxylic acid, p-toluenesulphonic acid and 1.6 g of sodium hydroxide in 40 ml of water and cool in ice. 1.70 g of benzyl chloroformate in 10 ml of acetone are added and allowed to return to room temperature overnight. The aqueous phase is washed twice with ether and then acidified to a pH of 2 using concentrated HCl. The white solid which precipitates is centrifuged, washed with water, then dried under a vacuum and triturated in an ether-pentane mixture (50/50; v/v) in order to obtain 3.05 g of the desired compound in the form of a white solid, F=142–144° C.

B) 1-Benzyloxycarbonyl-4-isocyanato-4-phenylpiperidine

Prepare a mixture containing 50.89 g of the acid prepared in the preceding stage and 71.4 g of thionyl chloride in 400 ml of 1,2-dichloroethane and bring to reflux up to the end of gaseous release. Evaporate under a vacuum, then recover in acetone and again evaporate to eliminate gaseous $SO_2$. Dissolve the oil obtained in 200 ml of acetone, cool to 5° C. in ice, then add at this temperature, drop by drop, 19.5 g of sodium azide in 60 ml of water. After 2 hours at room temperature, evaporate the acetone then extract with toluene and wash with a 5% solution of NaHCO₃, with water, and with a saturated solution of NaCl. Dry over Na₂SO₄, then evaporate the toluene to up to 30% of the initial volume and bring to reflux for 1 hour. As a result of evaporation to dryness, an orange oil is obtained which crystallizes to yield 54 g of the desired compound.

C) 1-Benzyloxycarbonyl-4-(N'-methylureido)-4-phenylpiperidine

Dissolve 25 g of the compound obtained in the preceding stage in 300 ml of ether and 300 ml of DCM and cool in ice, then bubble excess methylamine gas into the reaction mixture. After one night, the medium has partially crystallised. Evaporate to dryness, reheat in AcOET and then leave to crystallize at room temperature by adding a half volume of ether. 24 g of the desired compound are obtained in the form of white crystals.

D) 4-Phenyl-4-(N'-methylureido)piperidine Benzenesulphonate 23 g of the compound from the preceding stage are hydrogenated in the presence of 9.9 g of benzenesulphonic acid in 300 ml of EtOH 95 with 1 g of 5% Pd/C at 40° C. and at atmospheric pressure. Filter over Celite®—the catalyst, evaporate to dryness and take up the residue in acetone. 22.4 g of the desired compound are obtained, which crystallizes in the form of a white solid, F=227° C.

PREPARATION 3

4-Phenyl-4-ureidopiperidine Benzenesulphonate

This compound is prepared by proceeding in accordance with the operating method described in PREPARATION 2 by replacing methylamine gas by ammonia gas at stage C), F=235° C.

PREPARATION 4

4-(N',N'-Diethylureido)-4-phenylpiperidine p-Toluenesulphonate

A) 1-tert-Butoxycarbonyl-4-phenylpiperidine-4-carboxylic Acid

Place 100 g of 4-phenylpiperidine-4-carboxylic acid and p-toluenesulphonic acid in 800 ml of dioxane, add 150 ml of water and 109.7 g of K₂CO₃. Heat to 60° C. then add, drop by drop, 60.7 g of (Boc)₂0 in 100 ml of dioxane. Leave for 4 hours with stirring at 60° C. then heat under reflux for 1 hour. Evaporate to dryness, take up the solid formed in water, acidify to a pH of 3 by the addition of 2 N HCl, then add ether. Filter the crystals formed, wash them in water then in ether. Evaporate the etherified filtrate to dryness, take up the residue in ether and filter the crystals formed and add to those already obtained in order to dry them. 71 g of the desired compound are obtained.

B) 4-Isocyanato-4-phenyl-1-tert-butoxycarbonylpiperidine

Place 25 g of the acid obtained in the preceding stage in 100 ml of acetone and add 10.35 g of triethylamine. Cool in an ice bath then add, drop by drop, 8.7 g of methyl chloroformate in 30 ml of acetone and maintain the temperature at below 5° C. After 30 minutes, stirring in an ice bath, add 10.66 g of sodium azide drop by drop in 30 ml of water at a temperature below 5° C. and maintain stirring for 30 minutes, then pour over 500 ml of iced water. Extract 4 times using 130 ml of toluene, wash the organic phase twice with a pH 2 buffer using a saturated solution of NaCl and dry over MgSO₄. After filtration, heat the filtrate to 90° C. in an oil bath for 1 hour. Evaporate to dryness to yield 18.9 g of the desired compound.

C) 4-(N',N'-Diethylureido)-4-phenyl-1-(tert-butoxycarbonyl)piperidine

Place 6.05 g of the compound from the previous stage in 50 ml of acetone and add, drop by drop, 1.16 g of diethylamine in 3 ml of acetone at room temperature. Evaporate to dryness and then take up the residue in ether. Wash twice with a pH 2 buffer using a saturated solution of NaCl, then dry over MgSO₄ and evaporate to dryness. The residue is taken up in acetone and evaporated to dryness to yield 7.2 g of the desired compound.

D) 4-(N',N'-Diethylureido)-4-phenylpiperidine

Dissolve 7.1 g of the compound from the previous stage in 100 ml of MeOH and add 20 ml of concentrated HCl. Evaporate to dryness after one night of stirring at room temperature. Take up the residue in a 10% solution of NaOH and then extract 3 times in DCM. Wash the organic phase 3 times with a 10% solution of NaOH, then with a saturated solution of NaCl, dry over MgSO₄ and evaporate to dryness. 5.1 g of the desired compound are obtained.

E) 4-(N',N'-Diethylureido)-4-phenylpiperidine p-Toluenesulphonate

Place 5.1 g of the compound from the previous phase in 10 ml of acetone and add, drop by drop, 3.52 g of p-toluenesulphonic acid in 3 ml of acetone. Evaporate to dryness, then take up the residue with AcOEt. Add 5 ml of MeOH to the gum formed. Evaporate to dryness, then take up the residue in ET₂O and leave to stir overnight. Evaporate to dryness, then dry in the oven to yield 7.7 g of the desired compound; F=95° C. The intermediate compounds described in TABLE 1 below are prepared by following the operational method described in PREPARATION 4.

TABLE 1

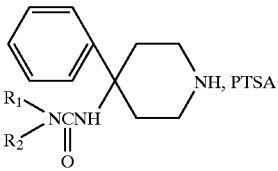

| PREPARATIONS | —NR₁R₂ | F°C |
|---|---|---|
| 5 | 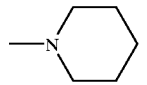 | 135 |
| 6 | 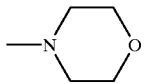 | 115 |
| 7 | | 93 |

PREPARATION 8

N-Methyl-N-(4-phenylpiperidin-4-yl)pyrrolidine-1-carboxamide

A) Benzyl Ester of 4-Phenyl-4-(pyrrolidin-1-ylcarbonylamino)piperidine-1-carboxylic Acid place 5 g of the compound obtained in PREPARATION 2, stage B, in 150 ml of ether and add 1.05 g of pyrrolidinene diluted in 25 ml of ether. Dilute with 100 ml of DCM, then stir for 30 minutes at room temperature. Evaporate to dryness, then take up in ether. Filter the product which crystallizes in order to obtain 5.23 g of the desired compound in the form of a white solid.

B) Benzyl Ester of 4-Phenyl-4-(pyrrolidin-1-ylcarbonyl-(N-methyl)amino)piperidine-1-carboxylic Acid In an ice bath, dissolve 2.5 g of the compound obtained from the previous stage in 10 ml of anhydrous THF. Add 4.9 ml of 1.5 M LDA in cyclohexane and allow to return to room temperature. Add, drop by drop, 0.8 ml of methyl iodide in 1 ml of THF and leave to stir overnight at room temperature. Evaporate, extract with ether and wash the organic phase in water, with 2 N HCl, with water, then with a 5% solution of $NaHCO_3$, with water and using a saturated solution of NaCl. Then dry the organic phase over $MgSO_4$, filter and evaporate to dryness. The oil obtained is chromatographed on silica by eluting with DCM then $DCM/CH_3CN$ (98/2; v/v). 1.3 g of the desired compound are obtained.

C) N-Methyl-N-(4-phenylpiperidin-4-yl)pyrrolidine-1-carboxamide

Dissolve 1.2 g of the compound obtained in the previous stage in 25 ml of EtOH and 25 ml of dimethoxyethane, then add 0.5 g of 5% Pd/C and hydrogenate at 40° C. under atmospheric pressure for 4 hours. Filter through Célite®, then evaporate the filtrate to dryness to obtain 0.75 g of the desired compound.

EXAMPLE 1

I, HCl: $-NR_3CONR_1R_2 = -NHCON(CH_3)_2$

Dissolve 3 g of 1-benzoyl-3-(3,4-dichlorophenyl)-3-(3-methane-sulphonyloxypropyl)piperidine, prepared in accordance with WO 97/10 211, in 5 ml of DMF. Add 2.2 g of $K_2CO_3$, then 1.897 g of 4-(N',N'-dimethylureido)-4-phenylpiperidine, the PREPARATION 1 salt-free compound. The reaction medium is heated whilst stirring for 2 hours at 80° C. in a flask topped with a $CaCl_2$ guard. Evaporate to dryness, extract with DCM, then wash the organic phase 3 times with a saturated solution of NaCl. Dry over $MgSO_4$, then evaporate and chromatograph the residue on H silica, eluting by means of DCM then DCM/methanol (100/2 to 95/5; v/v). Take up the residue in hydrochloric ether and centrifuge the precipitate formed. 1.318 g of the desired compound are obtained, F=165° C. with decomposition.

NMR: δ (ppm): 1.0 to 2.7: m: 12H; 2.7 to 4.5: m: 16H; 6.25: s: 1H; 7.0 to 7.9: m: 13H; 10.1: s: 1H.

Proceeding as in EXAMPLE 1, prepare the compounds in accordance with the invention set out in TABLE 2 by reacting 4-phenyl-4-ureidopiperidine in the form of p-toluenesulphonate, as obtained in the PREPARATIONS above, with 1-benzoyl-3-(3,4-dichlorophenyl)-3-(3-methanesulphonyloxypropyl)piperidine, either in racemic or in isomeric (+) form according to whether one wishes to obtain a compound (I) in racemic or isomeric (+) form.

TABLE 2

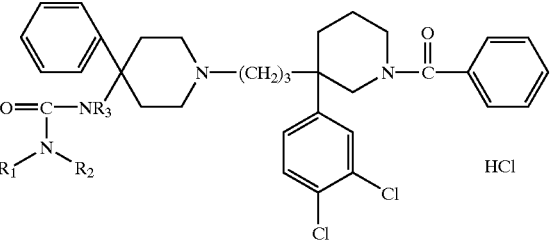

| Examples | $NR_3CONR_1R_2$ | F°C | racemic or $α_D$ |
|---|---|---|---|
| 2 | —NHCON(Et)₂ | 146 | racemic |
| 3 | —NHCON⟨pyrrolidinyl⟩ | 161 dec. | racemic |
| 4 | —NHCON⟨piperidinyl⟩ | 161 | racemic |
| 5 | —NHCON⟨piperidinyl⟩ | 156 | $α_D$ = +20.6° (c = 0.5; MeOH) |
| 6 | —NHCON⟨morpholinyl⟩ | 166 | racemic |
| 7 | —N(CH₃)CON⟨pyrrolidinyl⟩ | 94 | racemic |

NMR OF EXAMPLE 2

δ (ppm): 0.8 to 2.7: m: 18H; 2.7 to 4.4: m: 14H; 5.8 to 6.2: 2s: 1H; 7.0 to 7.8: m: 13H; 10.1: S: 1H.

NMR OF EXAMPLE 3

δ (ppm): 1.5 to 2.8: m: 16H; 2.8 to 4.5: m: 14H; 6.1: s: 1H; 7.0 to 7.8: m: 13H; 10.1: S: 1H.

NMR OF EXAMPLE 4

δ (ppm): 1.1 to 2.7: m: 18H; 2.5 to 4.5: m: 14H; 6.2 to 6.6: m: 1H; 7.0 to 7.8: 3s: 13H; 10.15: s: 1H.

NMR OF EXAMPLE 5

δ (ppm): 1.1 to 2.8: m: 18H; 2.8 to 4.5: m: 14H; 6.5: s: 1H; 7.1 to 7.9: m: 13H; 10.0: s: 1H.

NMR OF EXAMPLE 6

δ (ppm): 1.1 to 2.75: m: 12H; 2.75 to 4.5: m: 18H; 6.65: S: 1H; 7.05 to 7.8: m: 13H; 10.1: s: 1H.

NMR of EXAMPLE 7

δ (ppm): 1.1 to 4.5: m: 33H; 7.0 to 7.8: m: 13H; 10.0 to 10.9 : 2s: 1H.

EXAMPLE 8

1, HCl: $-NR_3CONR_1R_2=NHCONH_2$, (+) Isomer
A) 1-Benzoyl-3-(3,4-dichlorophenyl)-3-(2-formylethyl) piperidine, (+) Isomer.

Cool 5.24 g of oxalyl chloride in 75 ml of DCM under nitrogen to −60° C. Add, drop by drop, 8.05 g of DMSO in 10 ml of DCM at −60° C. and leave to stir for 10 minutes. Add, drop by drop, at −60° C., 13.5 g of 1-benzoyl-3-(3,4-dichlorophenyl)-3-(3-hydroxypropyl)piperidine, (+) isomer, prepared in accordance with EP-A-673 928, in 30 ml of DCM and 10 ml of DMSO. After 20 minutes of stirring, add 20.8 g of triethylamine at −50° C. and allow to return to room temperature for 1½ hours. Extract with DCM and then wash the organic phase with 2N HCl, water, a 5% solution of $NaHCO_3$, a saturated solution of NaCl, dry over $Na_2SO_4$ and evaporate under a vacuum. The desired product crystallizes from the pentane/ether mixture. F=102–104° C.

($\alpha_D$=+36.8° (c=0.5; MeOH)

B) 1-[3-[1-Benzoyl-3-(3,4-dichlorophenylpiperidin-3-yl]propyl]-4-phenylpiperidine-4-carboxylic Acid, (+) Isomer Mix 2.05 g of 4-phenylpiperidine-4-carboxylic acid and 3.9 g of the compound obtained in the preceding stage, in 50 ml of MeOH at room temperature; add 0.63 g of $NaBH_3CN$ and 5 ml of water then, drop by drop, 0.6 g of AcOH. After 2 hours, a white solid crystallizes. Centrifuge the crystals formed, wash in methanol, then in ether to obtain 3.8 g of the desired compound, F=244° C.

$\alpha_D$=+28.4° (c=0.5; DCM/MeOH: 50/50; v/v).

C) 1-Benzoyl-3-(3,4-dichlorophenyl)-3-[3-(4-isocyanato-4-phenylpiperid-1-yl)-1 Propyl]piperidine, (+) Isomer Reflux a mixture containing 5.79 g of the compound obtained in the preceding stage and 4.76 g of thionyl chloride in 100 ml of dichloroethane. After 2 hours, when no more gaseous release takes place, evaporate the reaction medium, then take up in acetone and evaporate under a vacuum. Dissolve the residue in 100 ml of acetone, cool in ice and then rapidly add 1.3 g of sodium azide in 15 ml of water. After 1 hour at room temperature, evaporate the acetone, then take up in a toluene/DCM mixture. Wash the organic phase with 2N NaOH, with a saturated solution of NaCl, dry over $Na_2SO_4$ and evaporate the DCM at 45° C., then bring to the toluene reflux for 30 minutes. The product obtained is used in the following stage as such.

D) Bubble gaseous ammonia in 100 ml of the toluenic solution obtained in the previous stage, cooled in an ice bath. After a few minutes, allow to return to room temperature, then, after 2 hours, evaporate the solvent, take up in water, then with AcOEt. Filter the precipitate, which forms between the two phases, then decant and wash the organic phase in water, with a 10% solution of $K_2CO_3$, water, and with a saturated solution of NaCl. Dry over $Na_2SO_4$ and evaporate. H silica chromatography is performed on the gum formed by eluting with DCM/MeOH from (98/2; v/v) to (95/5; v/v). Dissolve the product obtained in acetone, add a saturated solution of HCl gas in AcOEt and centrifuge the precipitate formed. 1.2 g of the desired compound are obtained in the form of a white solid, F=192–194° C.

$\alpha_D$=+22.82 (c=0.5; MeOH). NMR: δ (ppm): 1.0 to 2.6: m: 12H; 2.65 to 4.4: m: 10H; 5.5: s: 2H; 6.8: s: 1H; 7.0 to 7.8: m: 13H; 9.85: s: 1H.

EXAMPLE 9

I, HCl: —$NR_3CONR_1R_2$=—$NHCON(CH_3)OCH_3$, (+) Isomer

This compound is prepared in accordance with the process described in EXAMPLE 8, by reacting, at stage D, methoxymethylamine hydrochloride with the compound obtained in the preceding stage, F=165° C.

$\alpha_D$=+22° (c=0.5; MeOH). NMR: δ (ppm): 1.0 to 2.7: m: 12H; 2.7 to 4.4: m: 16H; 7.0 to 7.8: m: 13H; 10.35: s: 1H.

EXAMPLE 10

I, HCl: —$NR_3CONR_1R_2$=—$NHCON(CH_3)_2$, (+) Isomer

Dissolve 5.4 g of 4-(N',N'-dimethylureido)-4-phenylpiperidine p-toluenesulphonate obtained in PREPARATION 1 and 5 g of 1-benzoyl-3-(3,4-dichlorophenyl)-3-(2-formylethyl)piperidine, (+) isomer, obtained in EXAMPLE 8, stage A, in 50 ml of methanol. Add 0.7 ml of acetic acid, then, after 5 minutes, add 0.8 g of $NaBH_3CN$ in 10 ml of methanol and leave to stir overnight at room temperature, then pour the reaction mixture onto 150 ml of a 10% $Na_2CO_3$ solution. Extract with AcOEt, wash the organic phase with water, then dry over $MgSO_4$ and evaporate. The residue undergoes chromatography on H silica by eluting with DCM, then DCM/MeOH (100/1 to 100/7; v/v). The product obtained is taken up in hydrochloric ether and the crystals formed are centrifuged. 6.38 g of the expected compound are obtained.

$\alpha_D$=+22.9° (c=1; MeOH) NMR: δ (ppm): 1.1 to 2.7: m: 12H; 2.7 to 4.4: m: 16H; 6.25: s: 1H; 7.0 to 7.8: m: 13H; 10.4: s: 1H.

By following the operating method of EXAMPLE 10, configuration (R) compounds in accordance with the invention are prepared as described in TABLE 3:

TABLE 3

(I)

[Structure of compound I with piperidine rings, (CH2)3 linker, benzoyl group, 3,4-dichlorophenyl, NR3, NR1R2, HCl]

| Examples | $NR_3CONR_1R_2$ | racemic or $\alpha_D$ |
|---|---|---|
| 11 | —$NHONHCH_3$ | $\alpha_D$ = +23.3° (c = 1; MeOH) |
| 12 | —NHCON⟨morpholine⟩ | $\alpha_D$ = +20.9° (c = 1; MeOH) |

NMR OF EXAMPLE 11

δ (ppm): 1.0 to 2.6: m: 15H; 2.65 to 4.4: m: 10H; 6.0: s: 1H; 6.85: s: 1H; 7.0 to 7.8: m: 13H; 10.15: s: 1H.

NMR OF EXAMPLE 12

δ (ppm): 1.0 to 2.7: m: 12H; 2.5 to 4.4: m: 18H; 6.8: s: 1H; 6.9 to 7.75: m: 13H; 10.4: s: 1H.

EXAMPLE 13 I, HCl: —$NR_3CONR_1R_2$=NHCON$(CH_3)_2$, (−) Isomer

A) 1-Benzoyl-3-(3,4-dichlorophenyl)-3-(2-formylethyl)piperidine, (−) Isomer.

This compound is obtained from 1-benzoyl-3-(3,4-dichlorophenyl)-3-(3-hydroxypropyl)piperidine, (−) isomer, by following stage A of EXAMPLE 8.

$\alpha_D$=−35.8° (c=0.5; MeOH)

B) The desired compound is obtained by proceeding as in EXAMPLE 10.

$\alpha_D$=−21.6° (c=0.5; MeOH). NMR of EXAMPLE 13: δ (ppm): 1.1 to 2.8: m: 12H; 2.8 to 4.6: m: 16H; 6.3: s: 1H; 7.1 to 7.9: m: 13H; 10.1: s: 1H.

From the compound obtained in EXAMPLE 13, stage A, configuration (S) compounds in accordance with the invention described in TABLE 4 below are prepared.

TABLE 4

(I) [Structure: a compound with phenyl, piperidine linked via -(CH2)3- to a 3-(3,4-dichlorophenyl)piperidine with N-C(=O)-phenyl, and O=C-NR3 / N(R1)(R2) group; HCl salt]

| Examples | NR₃CONR₁R₂ | racemic or α_D |
|---|---|---|
| 14 | —NHCONH₂ | $\alpha_D = -26°$ (c = 0.5; MeOH) |
| 15 | —NHCONHCH₃ | $\alpha_D = -22.4°$ (c = 0.5; MeOH) |

NMR of EXAMPLE 14: δ (ppm): 1.05 to 2.6: m: 12H; 2.6 to 4.4: m: 10H; 5.5: se: 2H; 6.8: s: 1H; 7.0 to 7.8: m: 13H; 9.9: s: 1H.

NMR of EXAMPLE 15: δ (ppm): 1.0 to 2.6: m: 15H; 2.75 to 4.4: m: 10H; 5.9: s: 1H; 6.7: s: 1H; 7.0 to 7.8: m: 13H; 9.75: s: 1H.

EXAMPLE 16

(I): NR₃CONR₁R₂=NHCON(CH₃)₂, (+) Isomer

A)
(X): R₃=H; R'=tBu.

A mixture is prepared containing 300 ml of (+) 1-benzoyl-3-(3,4-dichlorophenyl)-3-(3-benzenesulphonyloxypropyl)piperidine, prepared in accordance with WO 97/10211, 110 ml of methyl isobutyl ketone and 28.8 g of the tert-butyl ester of (4-phenylpiperidin-4-yl)carbamic acid followed by the addition of 17.28 g of potassium carbonate and 17 ml of water with heating to 70° C. for 5 hours. The mixture is cooled to 50° C., then 270 ml of water are added and the mixture is allowed to return to room temperature. The organic phase is decanted, then dried on magnesium sulphate and concentrated. 69.82 g of the desired compound are obtained in the form of a yellow-coloured oil. HPLC purity: 90%.

NMR: 1.2 ppm: s: 9H; 1.8–2.4 ppm : m: 12H; 2.8–3.6 ppm: m: 10H; 7–7.6 ppm: m: 13H.

B)
(XI): R₃=H.

Mix 61 g of the compound from the preceding stage in solution in 200 ml of toluene and 120 ml of methyl isobutyl ketone, then add, over a period of 30 minutes, 39 ml of hydrochloric acid. Allow to return to room temperature, then stir for 1½ hours. The aqueous phase is extracted using 200 ml of AcOEt to which 49 ml of 10 N NaOH are then added. A double extraction is carried out using 200 ml of toluene and then the toluene phase is twice washed with 100 ml of water and 20 ml of concentrated HCl in 100 ml of water are added thereto. The aqueous phase is decanted and 22 ml of 10 N NaOH are added to it. The mixture is extracted with 200 ml of dichloromethane, dried over magnesium sulphate, filtered and concentrated. 49.4 g of the desired compound are obtained. HPLC purity: 96%.

NMR: 0.8–1.6 ppm: m: 12H; 2–3.6 ppm: m: 1OH; 7–7.6 ppm: m: 13H.

C)
A mixture is prepared containing 27.5 g of carbonyldiimidazole in 275 ml of DCM. This is cooled to -5° C. and to it is added a solution of 44.48 g of the compound from the preceding stage in 100 ml of DCM over a 45-minute period without exceeding 0° C. After stirring for 2 hours, 14.57 g of dimethylamine gas are added at -5° C. over a 20-minute period. The mixture is allowed to return to room temperature and then 350 ml of water are added. The organic phase is decanted and washed 3 times in 100 ml of water. Drying is over magnesium sulphate with filtration and concentration. 53.6 g of the desired compound are obtained in the form of a yellow-coloured oil. HPLC purity: 96.2%.

EXAMPLE 17

0.93 g of fumaric acid is dissolved under heat in 35 ml of ethanol and 5 g of the Example 16 compound in 15 ml of ethanol are added to this solution. After 15 minutes, the salt precipitates and the mixture is left to stir for 12 hours at room temperature. The salt formed is filtered, then washed with 10 ml of ethanol. Filtration is again undertaken with drying under a vacuum. 4.87 g of the desired compound are obtained. HPLC purity: 99%.

EXAMPLE 18

A solution of 5 g of the Example 16 compound in 10 ml of acetone is mixed with a solution of 0.9 g of succinic acid in 40 ml of acetone. After 12 hours of stirring at room temperature, the salt formed is filtered in order to obtain 4.87 g of the desired compound. HPLC purity: 98.2%.

EXAMPLE 19

A solution of 8.02 g of the compound of Example 16 in 25 ml of acetone and a solution of 1.57 g of benzoic acid in 15 ml of acetone are mixed. After 3 hours of stirring at room temperature, the salt formed is filtered, then dried under a vacuum at 50° C. to yield 7.48 g of the desired compound. HPLC purity: 99%.

EXAMPLE 20

A solution of 14.8 g of the compound of Example 16 in 30 ml of dichloromethane is prepared and acidified to a pH of 1 through the addition of a hydrochloric ether solution. After 30 minutes with stirring at room temperature, it is concentrated and taken up using 50 ml of isopropyl ether. The salt formed is filtered, then dried under a vacuum at 502C in order to obtain 13.94 g of the desired compound. HPLC purity: 94.5%.

EXAMPLE 21

| | |
|---|---|
| Example 16 compound | 25 mg |
| Pregelatinized starch | 78 mg |
| Lactose monohydrate | Q. S. |
| Magnesium stearate | 1.7 mg |
| for a No. 3 capsule filled to | 220 mg |

EXAMPLE 22

| | |
|---|---|
| Example 16 compound | 100 mg |
| Lactose monohydrate | Q. S. |
| Magnesium stearate | 1.7 mg |
| Purified water | Q. S. |
| for a No. 3 capsule filled to | 170 mg |

What is claimed is:
1. A compound of the formula:

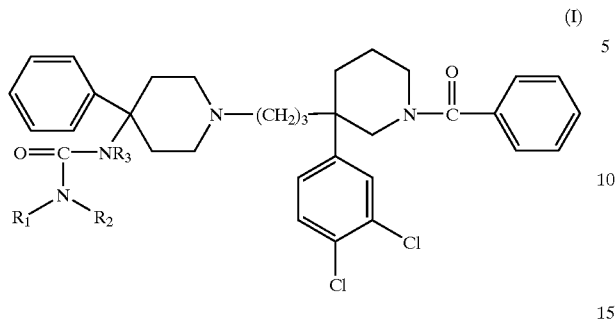

in which:
R$_1$ and R$_2$ each represent, independently of one another, hydrogen or a (C$_1$–C$_3$)alkyl;
or R$_1$ and R$_2$ together with the nitrogen atom to which they are bound constitute a heterocyclic radical selected from the group consisting of a pyrrolidin-1-yl, a piperidin-1-yl, and a morpholin-4-yl
or R$_1$ represents a methyl and R$_2$ represents a methoxy;
R$_3$ represents hydrogen or a (C$_1$–C$_3$)alkyl;
or an acid-addition salt or a solvate thereof.

2. A compound according to claim 1 in which R$_1$ and R$_2$ each independently represent hydrogen or a methyl.

3. A compound according to claim 1 in which R$_3$ represents hydrogen.

4. A compound according to claim 2 in the form of an (R) configuration (+) isomer.

5. 1-Benzoyl-3-(3,4-dichlorophenyl)-3-[3-[4-(N',N'-dimethylureido)-4-phenylpiperidin-1-]propyl]piperidine or an acid-addition salt or a solvate thereof.

6. 1-Benzoyl-3-(3,4-dichlorophenyl)-3-[3-[4-(N',N'-dimethylureido)-4-phenylpiperidin-1-]propyl]piperidine in the form of the (+) isomer or an acid-addition salt or a solvate thereof.

7. A process for the preparation of a compound according to claim 1 wherein:
a1) a compound of the formula:

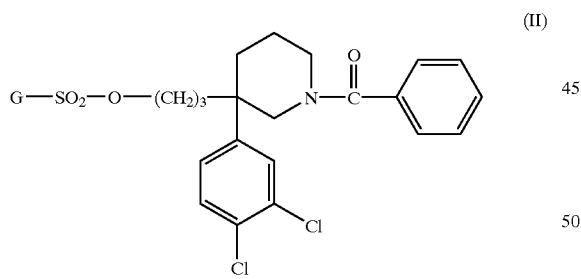

in which G represents a methyl, phenyl, tolyl or trifluoromethyl group is treated with a piperidine derivative of the formula:

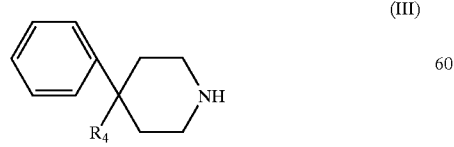

in which R$_4$ represents an NR$_3$CONR$_1$R$_2$ group or a COOH group, R$_1$, R$_2$ and R$_3$ being as defined in claim 1;

b1) when R$_4$=COOH the compound thus obtained of the formula:

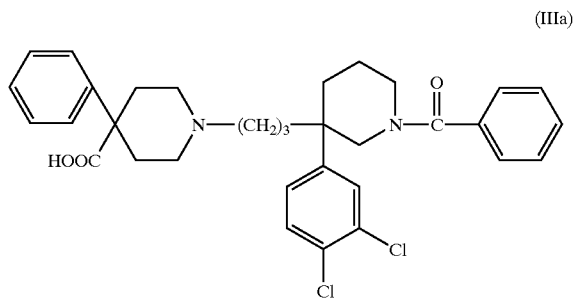

is converted to a compound according to claim 1;
c1) the compound thus obtained at stage a1) or stage b1) is optionally converted into one of its salts or solvates.

8. A process for the preparation of a compound according to claim 1 wherein:
a2) a compound of the formula:

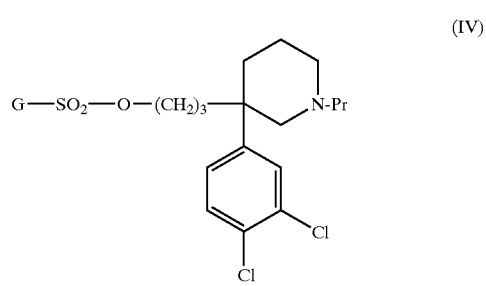

in which G is a methyl, phenyl, tolyl or trifluoromethyl group and Pr represents a protective group selected from the trityl, tert-butoxycarbonyl or benzyloxycarbonyl group is treated with a piperidine derivative of the formula:

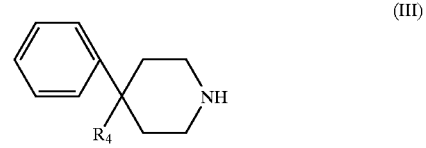

in which R$_4$ represents an NR$_3$CONR$_1$R$_2$ group or a COOH group, R$_1$, R$_2$ and R$_3$ being as defined in claim 1;
b2) the protective group Pr of the compound thus obtained of the formula:

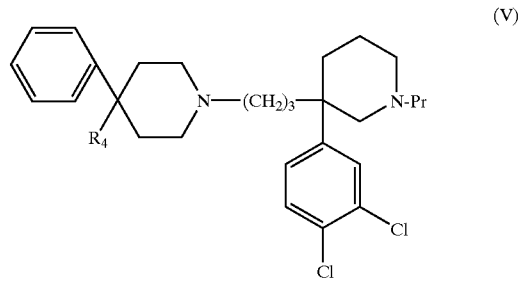

is selectively eliminated;

c2) the compound thus obtained of the formula:

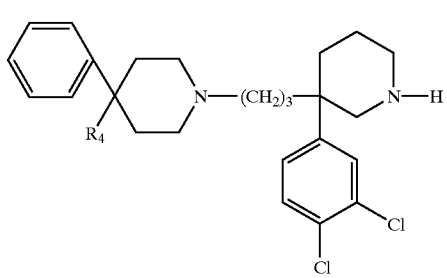

(VI)

is treated with a benzoyl halide;

d2) when the group $R_4$=COOH, the compound thus obtained of the formula:

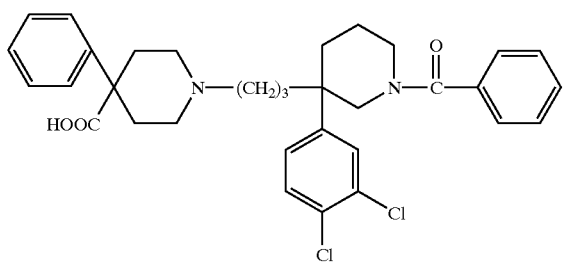

(IIIa)

is converted to a compound according to claim 1;

e2) the compound thus obtained at stage c2) or at stage d2) is optionally converted to one of its salts or solvates.

9. A process for the preparation of a compound according to claim 1 wherein:

a3) an alcohol of the formula:

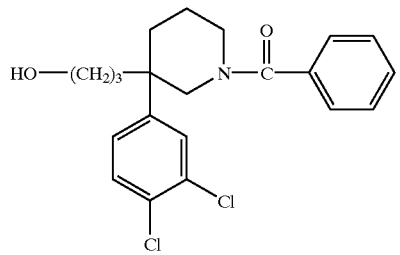

(VII)

is oxidized;

b3) the aldehyde thus obtained of the formula:

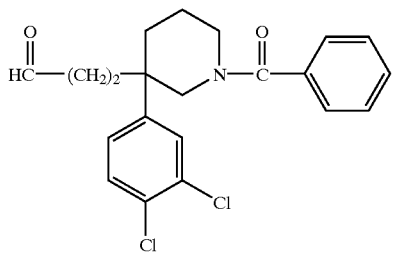

(VIII)

is treated with a piperidine derivative of the formula:

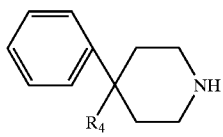

(III)

in which $R_4$ is $NR_3CONR_1R_2$ or COOH, $R_1$, $R_2$ and $R_3$ being as defined in claim 1;

c3) when $R_4$=COOH, the compound thus obtained of the formula:

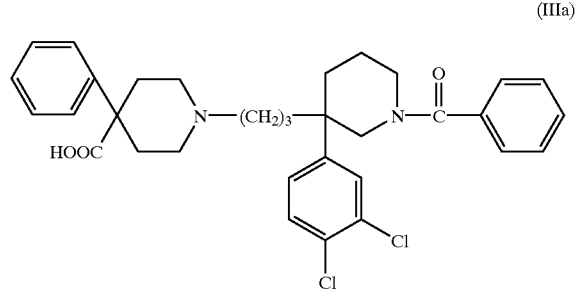

(IIIa)

is converted to a compound according to claim 1;

d3) the compound thus obtained at stage b3) or stage c3) is optionally converted into one of its salts or solvates.

10. A process for the preparation of a compound according to claim 1 wherein:

a4) a compound of the formula:

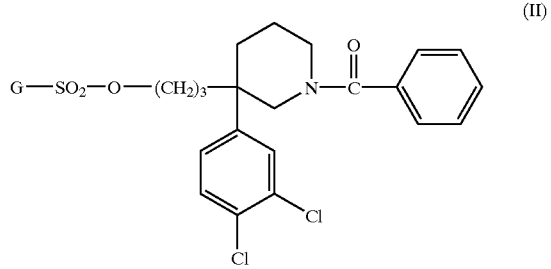

(II)

in which G is a methyl, phenyl, tolyl or trifluoromethyl group is treated, in the presence of a base, with the tert-butyl ester of (4-phenylpiperidin-4-yl)carbamic acid of the formula:

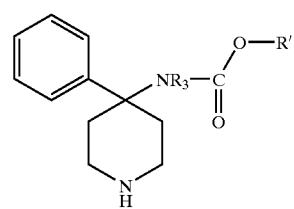

(IX)

in which R'=$(C_1-C_6)$alkyl and R3 is as defined in claim 1;

b4) the compound thus obtained of the formula:

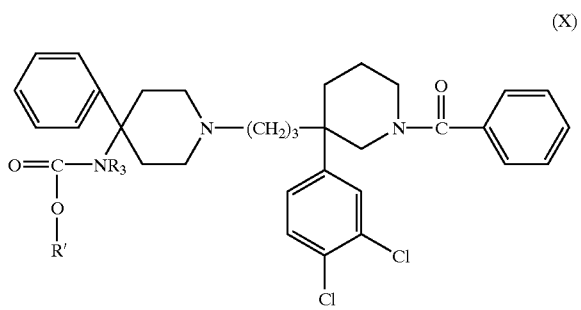
(X)

s deprotected by the action of an acid;
c4) the compound thus obtained of the formula:

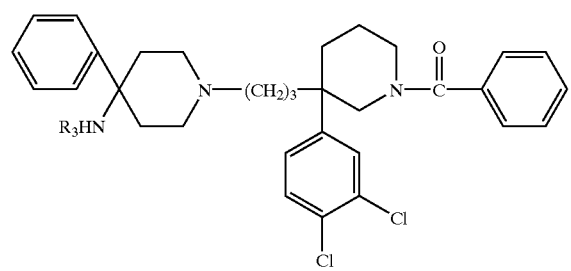
(XI)

is first treated by a reactive derivative of carbonic acid in the presence or absence of a base, then with an amine of the formula $NR_1R_2$ in order to obtain the desired compound according to claim 1.

11. A process according to claim 7 wherein a compound of the formula:

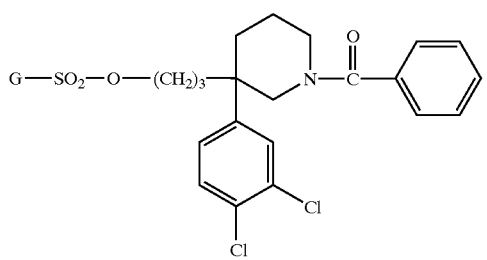
(II)

in which G is as defined in claim 7, is used, in the form of the (+) isomer, as the starting material.

12. A process according to claim 9 wherein an alcohol of the formula:

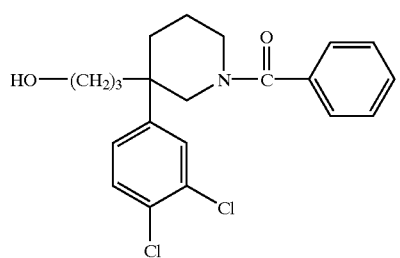
(VII)

in the form of the (+) isomer is used as the starting material.

13. A compound of the formula:

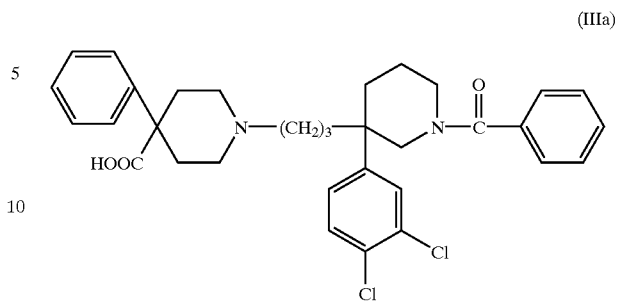
(IIIa)

in racemic form or in an optically pure form, or a salt thereof.

14. A pharmaceutical composition containing, as an active principle, a compound according to claim 1.

15. A compound according to claim 2 wherein $R_3$ is hydrogen.

16. A compound according to claim 3 in the form of an (R) configuration (+) isomer.

17. A compound according to claim 15 in the form of an (R) configuration (+) isomer.

18. A process according to claim 10 wherein a compound of the formula:

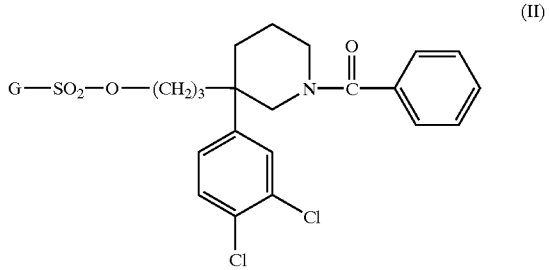
(II)

in which G is as defined in claim 10 is used in the form of the (+) isomer as the starting material.

19. A pharmaceutical composition containing, as an active principle, a compound according to claim 15.

20. A pharmaceutical composition containing, as an active principle, a compound according to claim 5.

21. A pharmaceutical composition containing, as an active principle, a compound according to claim 6.

22. A method for the treatment of pathologies in which neurokinin B and $NK_3$ receptors are involved which comprises administering to a patient in need of such treatment a therapeutically effective amount of a compound according to claim 1.

23. A method according to claim 22 for the treatment of respiratory disorders.

24. A method according to claim 22 for the treatment of central nervous system diseases.

25. A method according to claim 22 for the treatment of pain.

26. A method according to claim 22 for the treatment of gastrointestinal disorders.

27. A method for the treatment of pathologies in which neurokinin B and human $NK_3$ receptors are involved which comprises administering to a patient in need of such treatment a therapeutically effective amount of a compound according to claim 15.

28. A method according to claim 27 for the treatment of central nervous system diseases.

29. A method according to claim 27 for the treatment of respiratory disorders.

30. A method for the treatment of pathologies in which neurokinin B and human $NK_3$ receptors are involved which comprises administering to a patient in need of such treatment a therapeutically effective amount of a compound according to claim 5.

31. A method according to claim 30 for the treatment of central nervous system diseases.

32. A method according to claim 30 for the treatment of respiratory disorders.

33. A method for the treatment of pathologies in which neurokinin B and human $NK_3$ receptors are involved which comprises administering to a patient in need of such treatment a therapeutically effective amount of a compound according to claim 6.

34. A method according to claim 33 for the treatment of central nervous system diseases.

35. A method according to claim 33 for the treatment of respiratory disorders.

* * * * *